US00PP09473P

United States Patent [19]

Challet

[11] Patent Number: Plant 9,473

[45] Date of Patent: Mar. 12, 1996

[54] CHRYSANTHEMUM PLANT NAMED 'CHAPRILA'

[75] Inventor: Jean-Pierre Challet, Lafayette, Calif.

[73] Assignee: Selection New Plant Sarl, Le Cannet des Maures, France

[21] Appl. No.: 274,001

[22] Filed: Jul. 12, 1994

[51] Int. Cl.[6] ..... A01H 5/00

[52] U.S. Cl. ..... Plt./82.2

[58] Field of Search ..... Plt./82.2, 78

[56] References Cited

U.S. PATENT DOCUMENTS

| | | | |
|---|---|---|---|
| P.P. 6,774 | 5/1989 | VandenBerg | Plt./82.2 |
| P.P. 7,386 | 11/1990 | VandenBerg | Plt./82.2 |
| P.P. 7,453 | 2/1991 | VandenBerg | Plt./82.2 |
| P.P. 7,531 | 5/1991 | VandenBerg | Plt./82.2 |
| P.P. 7,847 | 3/1992 | VandenBerg | Plt./82.2 |
| P.P. 8,807 | 6/1994 | Polys | Plt./82.2 |
| 4,616,099 | 10/1986 | Sparkes | 47/58 |

OTHER PUBLICATIONS

Datta, 1991, "Evaluation of recurrent irradiation on vegetatively propagated ornamentals: Chrysanthemum", J. Nuclear Agric. Biol., 20(2):81–86.

Banerji, et al., 1990, "Induction of somatic mutation in chrysanthemum cultivar 'Anupani'", J. Nuclear Agric. Biol, 19:252–256.

Das, et al., 1977, "Improvement of some vegetatively propagated ornamentals by gamma radiation", Indian J. Hort., 34(2):169–174.

Gupta, et al., 1977, "Mutation breeding of chrysanthemums, II. Detection of gamma ray induced somatic mutations in vM2", J. Nuclear Agric Biol., 7(2):50–54.

Broertjies, et al., 1978, "Application of Mutation Breeding Methods in the Improvement of Vegetatively Propagated Crops", Elsevier Sci. Pub. Co., New York, pp. 162–175.

Glazurina, et al., 1977, "Use of the method of artificial mutagenesis in the breeding of flower crops", Cytology and Genetics, 11(3):42–45.

Broertjes, 1966, "Mutation breeding of chrysanthemums", Euphytica, 15:156–162.

*Primary Examiner*—Howard J. Locker

*Attorney, Agent, or Firm*—Burns, Doane, Swecker & Mathis

[57] ABSTRACT

A new and distinct Chrysanthemum cultivar named 'Chaprila' is provided. The new cultivar is a mutation of the 'Chakara' cultivar (U.S. Plant Pat. Application Ser. No. 08/273,994, filed Jul. 12, 1994) that was created through gamma irradiation. Attractive golden yellow anemone blossoms are formed in profusion as a round ball surrounding the plant (as illustrated). The response period of the flowers is approximately eight weeks. Recurrent flower production throughout the year is possible. The plant possesses strong stems, forms attractive leaves, and commonly assumes a height of approximately 30 to 35 cm. The new cultivar is particularly suited for use in the production of a decorative pot Chrysanthemum. No growth regulator is required to achieve the short plant height.

4 Drawing Sheets

SUMMARY OF THE INVENTION

The present invention comprises a new and distinct cultivar of Chrysanthemum, botanically known as *Dendranthema grandiflora,* and hereinafter is referred to by the cultivar name 'Chaprila'.

The new cultivar of the present invention was created through the gamma irradiation of the 'Chakara' cultivar (U.S. Plant Patent Application Ser. No. 08/273,994, filed Jul. 12, 1994). The parent 'Chakara' cultivar was formed by the crossing of the 'Fada' cultivar (non-patented in the United States) and the 'Domi' cultivar (non-patented in the United States) as described in my copending U.S. Patent Application.

During June 1988, at Saint Paul Lez Durance, France, groups of 1,000 rooted cuttings of the 'Chakara' cultivar having an age of two weeks were irradiated with gamma rays through the packing boxes at rates of 1.8, 2.5 and 3.0 Krads. Following irradiation the plants were shipped to Nuaille, Trementines, France, and planted in 4 liter pots, pinched, and grown outside until September, next grown in greenhouses, were not disbudded, and were carefully observed. It was found that most of the plants irradiated at a rate of 3.0 Krads died. Those plants that were irradiated at a rate 2.5 Krads exhibited no growth following pinching and were discarded. Many different mutations were observed in the plants that were irradiated at a rate of 1.8 Krads. A single mutation that exhibits the characteristics of the 'Chaprila' cultivar was discovered among these plants. Also, a single cultivar that exhibits the characteristics of the 'Chaplou' cultivar (U.S. Plant Patent Application Ser. No. 08/273,992, filed Jul. 12, 1995) was discovered among the same group of plants. It would have been impossible for a plant scientist to have predicted in advance that new cultivars having the combination of characteristics of the presently claimed 'Chaprila' cultivar and the sister 'Chaplou' cultivar could have been formed even if the parent 'Chakara' cultivar would have been available for such experimentation.

It was found that the new 'Chaprila' cultivar of the present invention:

(a) exhibits in profusion attractive large golden yellow anemone blossoms, (b) exhibits a flower response period of approximately eight weeks, (c) is highly amenable to branching by pinching, (d) achieves a short plant height, and (e) is particularly suited for pot mum production on a recurrent basis throughout the year.

The new cultivar is intended for use primarily as a decorative pot anemone spray Chrysanthemum for growing indoors. However, the new cultivar can be grown outdoors at temperatures above freezing.

In the absence of debudding a profusion of blossoms form per stem (as illustrated). The new cultivar can also be grown as a disbud to form striking blooms. A greatly increased number of branches readily can be induced by pinching. The pinching of a cutting commonly produces 5 or more stems.

No growth regulator is required to produce the short plant height.

The new cultivar can be considered to be an October-flowering greenhouse variety with the natural flowering season commonly occurring in weeks 41 and 42 of the year. Attractive blossoms can be produced on a recurrent basis throughout the year with the indicated eight week response period. The blossoms commonly last approximately two weeks on the plant, and commonly less than one week when placed in a vase.

Night temperatures above approximately 23° C. will delay flowering. Night temperatures as low as 14° C. generally can be well tolerated, and night temperatures as low as 5° to 10° C. can be tolerated at the bud-cracking stage.

Asexual reproduction of the new cultivar by cuttings initially taken during 1991, as performed in Nuaille, Trementines, France, in a controlled environment has demonstrated that the characteristics of the new cultivar as herein described are firmly fixed and are retained through successive generations of asexual propagation.

'Chaprila' has not been observed under all possible environmental conditions to date. Accordingly, it is possible that the phenotype may vary somewhat with variations in the environment, such as temperature, light, day length, contact with pesticides and/or subjection to growth retardant treatments.

The 'Chaprila' cultivar of the present invention can be readily distinguished from its parent. More specifically, the 'Chaprila' cultivar exhibits a golden yellow capitulum unlike the bright bronze capitulum of the 'Chakara' cultivar, a stem coloration of Yellow-Green Group 146C instead of Yellow-Green 144A for the 'Chakara' cultivar, anthocyanin coloration only at the ribs unlike the 'Chakara' cultivar, an angular stem cross section unlike the round stem cross section of the 'Chakara' cultivar, a slightly lesser degeee of coarseness in the leaf serration than the 'Chakara' cultivar, an upper leaf surface coloration of between Green Group 137C and Yellow-Green Group 146B that generally can be distinguished from the coloration of Green Group 137B to 137C for the 'Chakara' cultivar, parallel margins of sinus between lateral leaf lobes unlike the converging margins of the 'Chakara' cultivar, a mucronate leaf apex unlike the cuspidate leaf apx of the 'Chakara' variety, a weakly convex ray floret cross section unlike the generally flat ray floret cross section of the 'Chakara' cultivar, and a long day leaf count of approximately 17 to 19 unlike the 17 to 22 count commonly exhibited by the 'Chakara' cultivar.

Also, the 'Chaprila' cultivar of the present invention can be readily distinguished from its sister 'Chaplou' cultivar. More specifically, the 'Chaprila' cultivar exhibits a golden yellow capitulum unlike the red bronze capitulum of the 'Chaplou' cultivar, a stem coloration of Yellow-Green Group 146C instead of Yellow-Green Group 146D for the 'Chaplou' cultivar, anthocyanin coloration only at the ribs unlike the 'Chaplou' cultivar, a coarser leaf serration than the 'Chaplou' cultivar, an upper leaf surface coloration between Green Group 137C and Yellow-Green Group 146B unlike the coloration of Yellow-Green Group 144A for the 'Chaplou' cultivar, presence of a claw in the base of the sinus between lateral leaf lobes unlike the 'Chaplou' cultivar, parallel margins of sinus between leaf lobes unlike the converging margins of the 'Chaplou' cultivar, a weakly convex ray floret cross section unlike the concave ray floret cross section of the 'Chaplou' cultivar, and a long day leaf count of approximately 17 to 19 unlike the 15 to 19 count commonly exhibited by the 'Chaplou' cultivar.

The new 'Chaprila' cultivar of the present invention is being marketed under the Venus trademark.

BRIEF DESCRIPTION OF THE PHOTOGRAPHS

The accompanying photographs were prepared during June, 1994, and show as nearly true as it is reasonably possible to make the same in color illustrations of this character, typical plants and plant parts of the new cultivar of the present invention. The plants were 13 weeks of age and were grown at Nuaille, Trementines, France, under standard greenhouse conditions which approximate those commonly utilized for the production of decorative pot mums. The plants had been pinched once and had not been disbudded. No growth regulant was utilized. Any labels shown in the photographs are 2.5 cm. in width and can be used for size comparisons.

DETAILED DESCRIPTION

Figure 1:
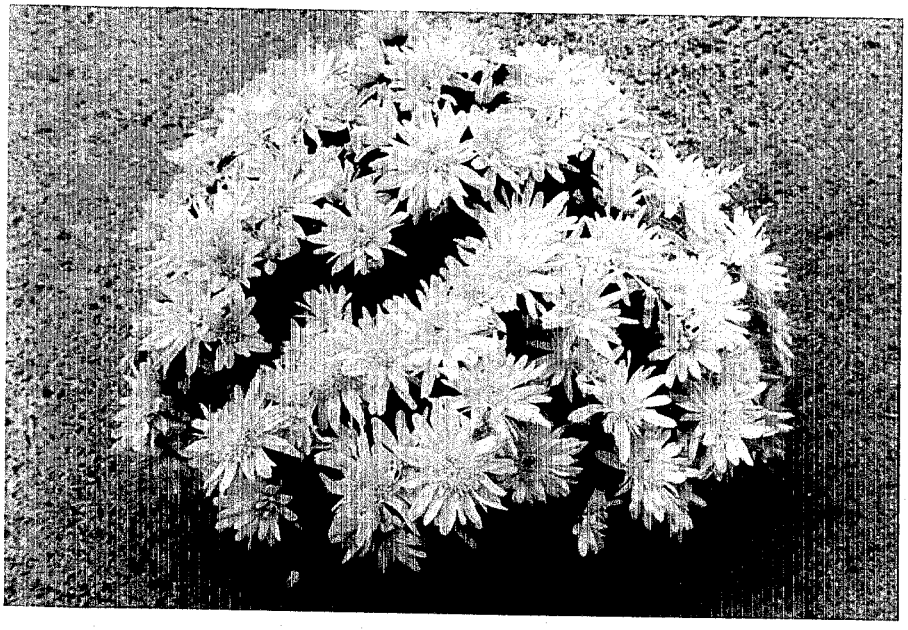
FIG. 1 illustrates typical specimens of the overall plant wherein three cuttings were placed in a 20 cm. pot. The golden yellow anemone flowers that are displayed as a round ball surrounding the plant, as well as the foliage, are apparent.
Figure 2:
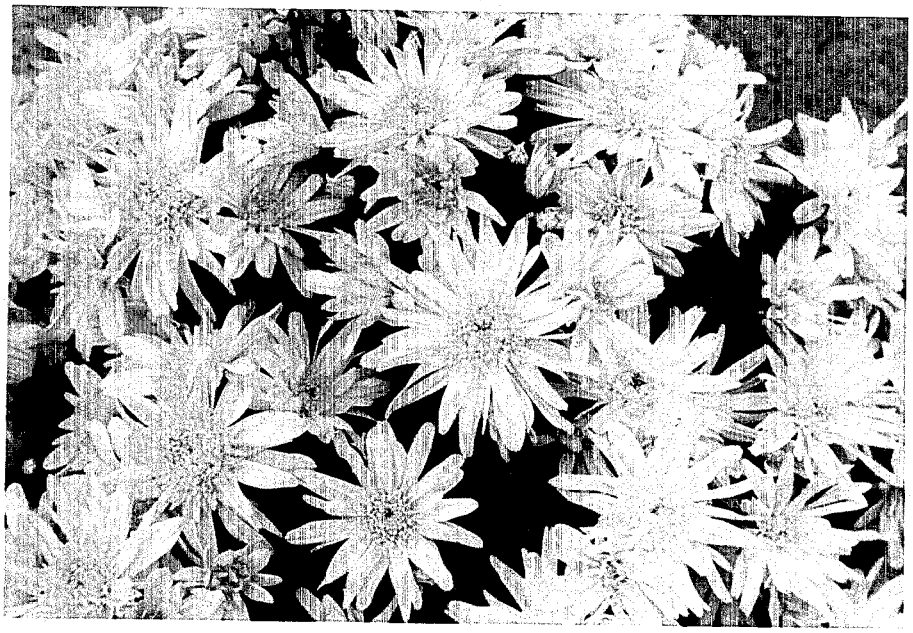
FIG. 2 illustrates a closer view of typical golden yellow blossoms when fully open wherein some fading of the coloration has taken place.
Figure 3:
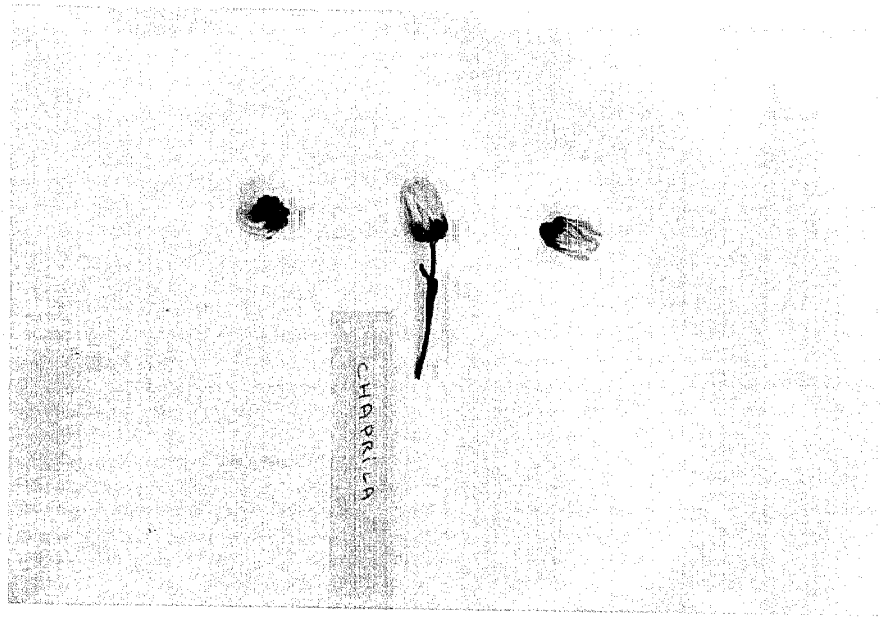
FIG. 3 illustrates from left to right, upper, side, and under views of largely unopened buds.
Figure 4:
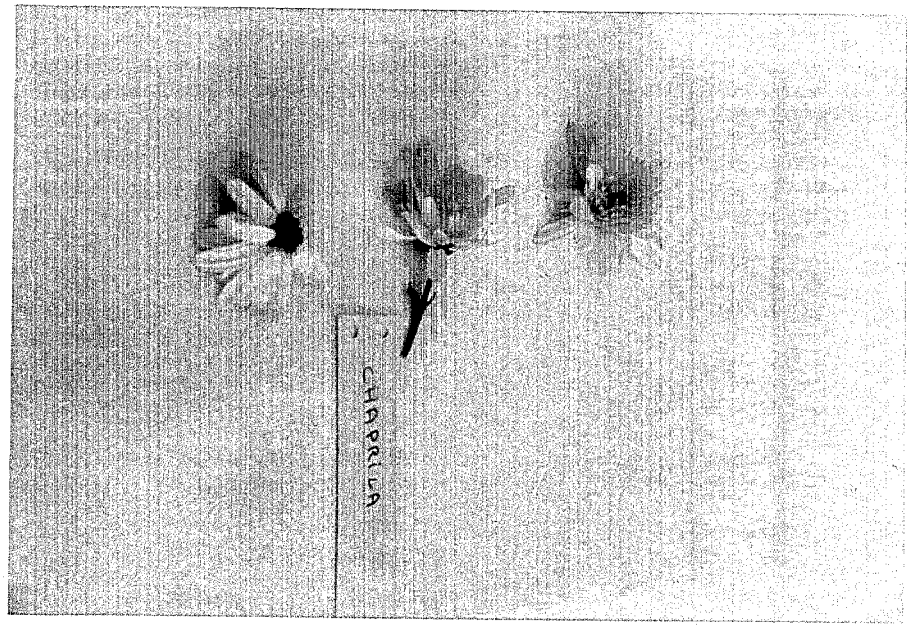
FIG. 4 illustrates from left to right, under, side, and top views of buds in the course of opening.
Figure 5:
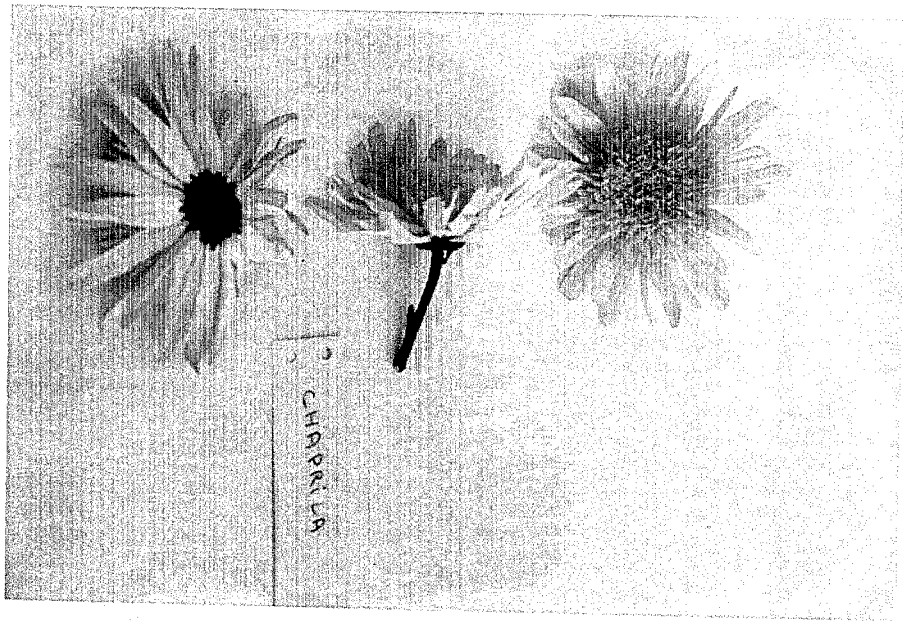
FIG. 5 illustrates from left to right, under, side, and upper views of newly opened flowers. The darker blossom coloration that commonly is present when the blossoms are immature is visible.
Figure 6:
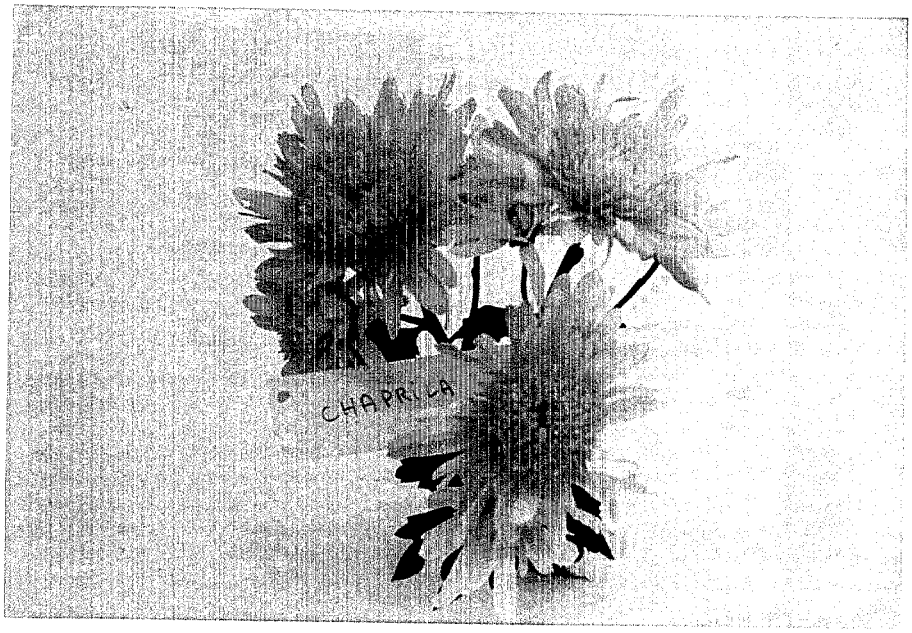
FIG. 6 illustrates a typical cluster of newly opened flowers wherein the darker coloration that is present when the blossoms are immature is visible.
Figure 7:
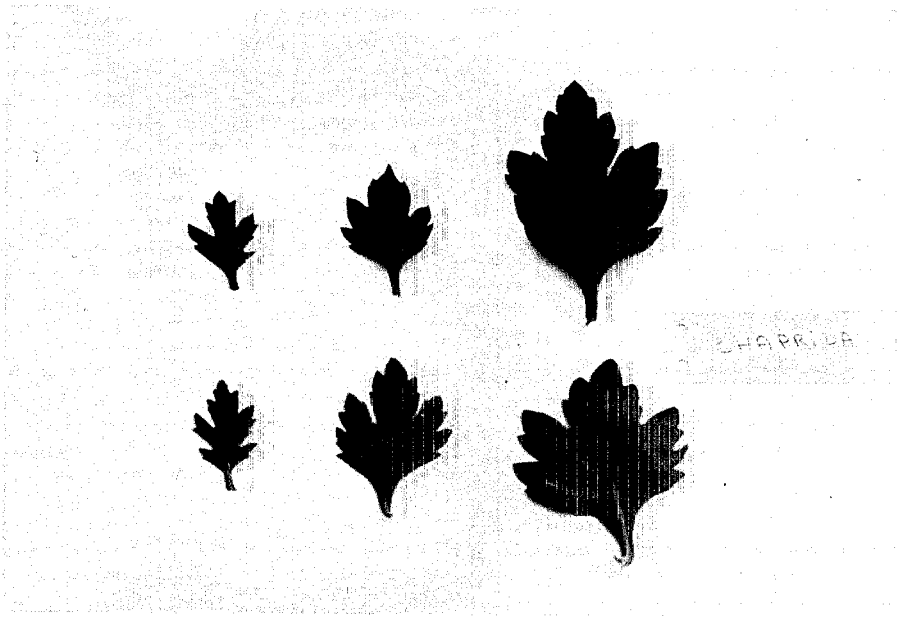
FIG. 7 illustrates at the top row the upper surfaces of typical leaves of various sizes, and at the bottom row the under surfaces of typical leaves of various sizes.

The chart used in the identification of colors described hereafter is the R.H.S. Colour Chart of The Royal Horticultural Society, London, England. In some instances more common color terms are provided and are to be accorded their usual dictionary significance. The plants described were 13 weeks of age and were grown at Nuaille, Trementines, France, under standard greenhouse conditions which proximate those commonly utilized for the production of decorative pot mums.

Classification:

*Botanical.*—*Dendranthema grandiflora,* cv. 'Chaprila'.

*Commercial.*—Decorative pot mum.

Inflorescence

A. Capitulum:

*Type.*—Anemone.

*Diameter across face.*—Medium, approximately 9 to 10 cm. on average when fully expanded.

*Frequency.*—Corymbiform, and blossoms form in profusion (as illustrated).

*Outside bud coloration.*—Near Greyed-Orange Group 163B deepening to Greyed-Orange Group 163A towards the tip.

B. Corolla of ray and disc florets:

*Disc florets.*—Petaloid, numerous, very long, massed and clearly visible at all stages of flower head development, and commonly form a disc of approximately 4.5 cm. in diameter.

*General tonality.*—Golden yellow capitulum that tends to fade somewhat as the blossoms fully mature (as illustrated). As the blossoms mature, some brightness of coloration commonly is lost.

*Color of disc florets.*—Before dehiscence, Yellow-Orange Group 14A commonly with some Yellow-Green Group 1B towards the tip. After anther dehiscence, Yellow Group 13C on the outside and near Yellow Group 13A on the inside with slightly more red.

*Color ray florets.*—The inner surfaces commonly are near Yellow Group 13A but slightly more red. The outer surfaces commonly are Yellow Group 7C at the extreme base and merging elsewhere to Yellow-Orange Group 13B but more red. The color is best and brighter when the plant is finished cool, since the plant generally does not well tolerate high levels of heat. The coloration tends to fade somewhat (as illustrated) as the blossoms mature.

*Configuration ray florets.*—Weakly convex in cross section, rough in texture, generally straight, and possess dentated tips, and sometimes mamillate tips.

C. Reproductive organs:

*Androecium.*—Generally present with disc florets and absent in ray florets.

*Gynoecium.*—Generally present with most disc florets and with most ray florets.

*Pollen.*—Generally present in a relatively large quantity, and golden-yellow in coloration.

*Fragrance.*—Typical of Chrysanthemum.

Plant

A. General appearance:

*Height.*—Short, and approximately 30 to 35 cm. in height on average at 10 weeks of age. The exact height is influenced by the growing conditions.

*Growth habit.*—Normal.

B. Foliage

*Color (upper surface).*—Commonly between Green Group 137C and Yellow-Green Group 146B.

*Color (under surface).*—Generally slightly lighter green than upper surface (as illustrated).

*Long day leaf count.*—Approximately 17 to 19 leaves per typical stem in a long day crop before the bud occurs.

*Configuration.*—Very short and lobed (as illustrated).

*Texture.*—Fleshy.

*Serration.*—Medium to medium to coarse.

*Shape of base.*—Asymmetric and tending to be rounded and occasionally truncate.

*Apex.*—Mucronate.

*Internode length.*—Very short.

*Stems.*—Thin, strong, angular in cross section, Yellow-Green Group 146C in coloration, and commonly with anthocyanin coloration only at the ribs.

*Claw in base of sinus between lateral lobes.*—Present.

*Margins of sinus between lateral lobes.*—Parallel.

I claim:

1. A new and distinct cultivar of Chrysanthemum plant named 'Chaprila', substantially as herein shown and described, which (a) exhibits in profusion attractive large golden yellow anemone blossoms, (b) exhibits a flower response period of approximately eight weeks, (c) is highly amenable to branching by pinching, (d) achieves a short plant height, and (e) is particularly suited for pot mum production on a recurrent basis throughout the year.

* * * * *